United States Patent [19]
Doctor et al.

[11] Patent Number: 5,267,945
[45] Date of Patent: Dec. 7, 1993

[54] FINGER SPLINT FOR TREATING PIP JOINT INJURIES

[76] Inventors: David Doctor, 515 W. 59th St., Apt. 9K, New York, N.Y. 10019; Jonathan Doctor, 90 Morningside Dr., South, Greens Farms, Conn. 06436

[21] Appl. No.: 690,589

[22] Filed: Apr. 24, 1991

[51] Int. Cl.⁵ .................. A61F 7/00; A61F 5/04
[52] U.S. Cl. .................... 602/14; 602/22; 602/30
[58] Field of Search .......... 128/77, 87 A, 87 R, 128/90, 402, 403; 602/21, 22, 63, 5, 14, 30

[56] References Cited

U.S. PATENT DOCUMENTS

| | | | |
|---|---|---|---|
| 1,817,212 | 8/1931 | Siebrandt | 602/21 |
| 2,022,883 | 12/1935 | Gee | 602/5 |
| 2,074,113 | 3/1937 | Hovey | 128/880 |
| 2,523,606 | 9/1950 | Young | 128/90 |
| 3,039,460 | 6/1962 | Chandler | 128/87 A |
| 3,086,529 | 4/1963 | Munz et al. | 128/878 |
| 3,306,288 | 2/1967 | Rosenfield | 602/63 X |
| 3,774,242 | 11/1973 | Owen | 2/158 |
| 4,055,188 | 10/1977 | Pelton | 128/403 X |
| 4,167,044 | 9/1979 | Girard | 128/77 |
| 4,204,534 | 5/1980 | Leary | 128/878 |
| 4,270,528 | 6/1981 | Hanson | 128/87 A |
| 4,445,507 | 5/1984 | Eisenberg | 128/87 A |
| 4,524,646 | 6/1985 | Primiano et al. | 128/87 A |
| 4,531,735 | 7/1985 | Kovacs | 128/87 A |
| 4,556,055 | 12/1985 | Bonner, Jr. | 128/82.1 |
| 4,565,195 | 1/1986 | Eisenberg | 128/165 |
| 4,615,046 | 10/1986 | Martin | 128/77 X |
| 4,625,729 | 12/1986 | Roney | 128/403 X |
| 4,644,941 | 2/1987 | Ogle, II | 602/22 |
| 4,645,498 | 2/1987 | Kosak | 128/403 X |
| 4,653,490 | 3/1987 | Eisenberg | 128/87 A |
| 4,753,240 | 6/1988 | Sparks | 128/402 X |
| 4,781,178 | 11/1988 | Gordon | 128/87 X |
| 4,953,568 | 9/1990 | Theisler | 128/878 |
| 4,966,137 | 10/1990 | Davini | 128/87 R |
| 5,095,897 | 3/1992 | Clark et al. | 602/22 |

FOREIGN PATENT DOCUMENTS

| | | | |
|---|---|---|---|
| 2578740 | 9/1986 | France . | |
| 2094152 | 9/1982 | United Kingdom | 128/87 A |
| 9000378 | 1/1990 | World Int. Prop. O. | 128/87 R |

*Primary Examiner*—Mickey Yu
*Assistant Examiner*—Brian E. Hanlon
*Attorney, Agent, or Firm*—Ostrolenk, Faber, Gerb & Soffen

[57] ABSTRACT

The finger splint includes an elastic sleeve for enclosing a finger with an injured joint. The sleeve is tapered slightly to conform to the shape of the finger. A gel pack is incorporated into the sleeve to either heat or cool the injured joint. A strap is attached at each end of the sleeve, to be wrapped around the adjacent uninjured finger to hold the injured finger to the adjacent finger, while permitting normal active motion of the fingers. Velcro (TM) patches are provided to secure the straps to hold the two fingers together.

6 Claims, 2 Drawing Sheets

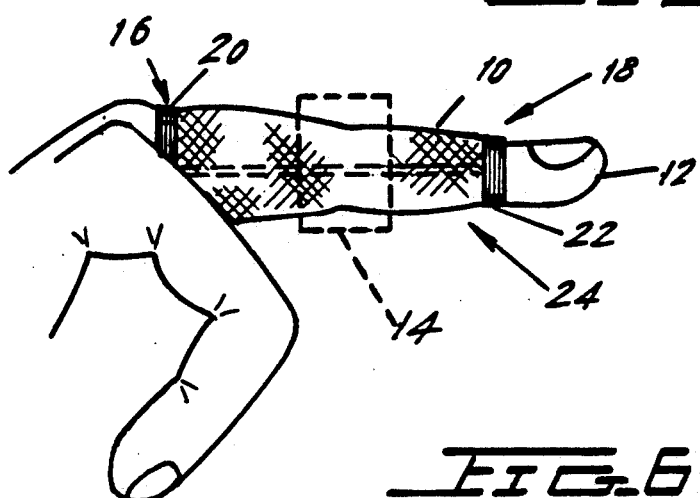
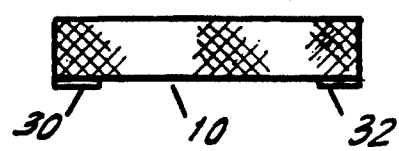
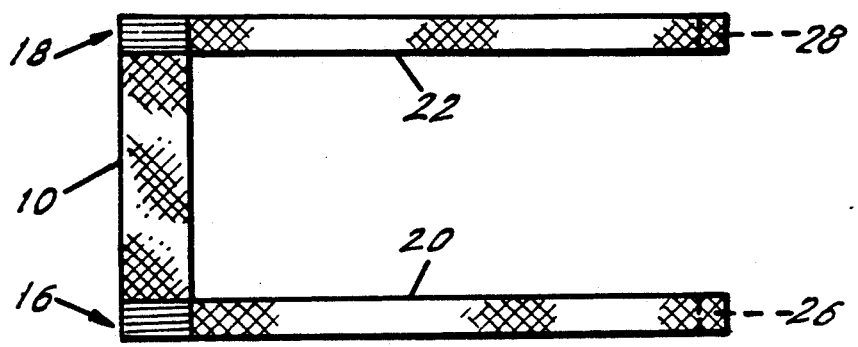
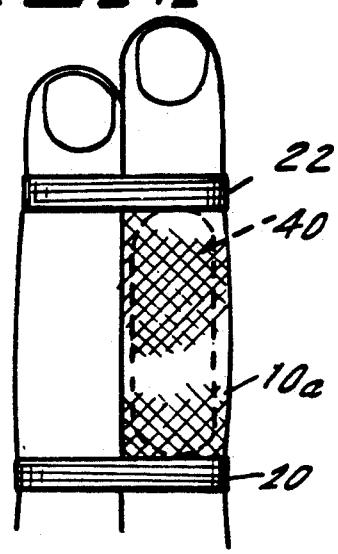
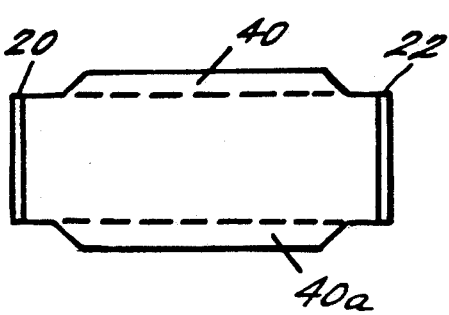

FINGER SPLINT FOR TREATING PIP JOINT INJURIES

FIELD OF THE INVENTION

The invention relates to a finger splint, and more particularly to a finger splint which may include an elastic sleeve for enclosing an injured finger, attachments to hold the finger to an adjacent uninjured finger, and a gel material to either heat or cool the finger.

BACKGROUND ART

Each finger (except the thumb) contains three bony segments and three joints which permit bending (flexion) and straightening (extension) about each joint (FIGS. 1-2). The second joint is called the proximal interphalangeal joint or PIP joint. The PIP joints of the index through small fingers, especially the ring and long fingers, are among the most commonly injured joints in the hand. During recreational activities an individual often holds his or her finger out straight in the fully extended position. If it is then struck on the tip by an object such as a football, a swinging door or a dropping weight, the result is the classic "jammed finger," characterized by a variable amount of swelling around the joint and considerable pain and stiffness when trying to bend the finger.

The anatomy of this injury is fairly simple: the PIP joint is held together by ligaments which traverse the joint and attach to the bony segments on either side of the joint. The collateral ligaments are the structures which prevent side-to-side motion of the joint and only permit normal flexion and extension. Thus when the extended finger is suddenly struck by an object and forced to one side or the other, this is the ligament that will tear (FIG. 3). The "jammed finger", therefore, is a sprain or partial tear of a collateral ligament of the PIP joint. This is the injury that is principally addressed by the present invention.

Partial tears probably make up greater than 95% of all PIP ligament injuries All partial tears or sprains of collateral ligaments are currently treated with the method known as "buddy-taping" (FIG. 4). The injured finger is taped to a normal adjacent digit and active motion is encouraged from the outset. The tape is worn continuously for three weeks, and then during periods of anticipated stress for an additional three weeks. Usually athletes can play during the entire period of treatment. While a PIP sprain is not a serious injury, the pain and swelling will persist for weeks and often months, and normal function of the joint does not return for several months or even up to one year. Many people either do not seek treatment or treat the injury themselves, because they believe the injury is not serious and they resist going to a physician unnecessarily. Others, concerned that something is broken, will go to their doctor or to a nearby Emergency room, only to discover that the X-rays are negative and the injury is not as serious as they had thought. Both groups of people could benefit from an improved and simplified method and dressing for treating this injury.

The current method of buddy-taping, with standard cloth tape available in most Emergency departments and drug stores, often does not hold up to persistent activity during the recommended three to six weeks of total treatment time. The tape often falls apart and many patients will not replace the tape when this occurs because it is inconvenient to retape and there is no suitable alternative. People who don't seek treatment for the sprain might try splinting the finger with some stiff, bulky material at home such as an emery board. This quickly becomes a nuisance and is discarded. It also prevents active movement of the joint, which is desirable during the treatment of the injury.

The preferred treatment during the acute period of the injury, i.e., the first 24-48 hrs., also includes application of cold. Unfortunately, icing a single finger with a large ice pack is often difficult and inconvenient.

Various finger and hand splints are known to the art, but none of these is well adapted for treating PIP joint injuries.

Rigid finger splints are shown in U.S. Pat. No. 4,781,178 to Gordon, U.S. Pat. No. 3,039,460 to Chandler, U.S. Pat. No. 2,022,883 to Gee, U.S. Pat. No. 2,523,606 to Young, U.S. Pat. No. 1,817,212 to Siebrandt and French patent 2,578,740. These splints prevent active movement of the finger, and so are not usable for treating PIP joint injuries.

U.S. Pat. No. 4,953,568 to Theisler discloses an adjustable thumb brace for restraining an injured thumb A resilient band fit around the palm of the hand and is tightened by Velcro-secured straps. Thumb braces of this type are not usable to support the index through fourth fingers to treat a PIP joint injury.

None of the known references discloses or suggests a convenient dressing for treating PIP joint injuries, so as to improve upon the conventional "buddy-taping." Nor do the references suggest a convenient means of applying a cold compress to such an injury.

SUMMARY OF THE INVENTION

The present invention offers a successful alternative to the currently accepted buddy-taping methods and to makeshift household splinting. It provides a comfortable support for the injured joint and is easily worn for the duration of treatment, while allowing active range of motion of the joint. It can be provided with a built-in chemical pack as part of a sleeve for the finger, so only the injured finger will be iced (or heated) while the sleeve is worn.

To accomplish these objects, a finger splint for treating PIP joint injuries comprises an elastic sleeve sized for splinting a given finger with the PIP joint near a middle portion of the sleeve; a pair of straps on the sleeve having two ends and being sized for extending from the sleeve on both sides of the PIP joint, around an adjacent finger, and back to the sleeve; and fastening arrangements associated with the sleeve and the straps for fastening both ends of the straps to the sleeve. Such straps coact to securely hold the splinted finger to the adjacent finger, while permitting active motion of the splinted finger. Each strap is permanently attached to the sleeve at one end, and an easily releasable fastener such as a hook-and-loop-type fastener is provided for attaching the other end to the sleeve.

Advantageously, the sleeve also has a flexible heat- and cold-retaining material in substantial contact with said splinted finger. The material may be a fluid or gel contained in a flexible pouch on the sleeve, in contact at least with the back or front, or both, of said splinted finger.

Other features and advantages of the present invention will become apparent from the following description of embodiments of the invention, with reference to the accompanying drawings.

BRIEF DESCRIPTION OF THE DRAWINGS

FIG. 5 is a side view of an injured finger which is being treated by a dressing according to a first embodiment of the invention;

FIGS. 6A and 6B are respectively a top view and a side view of the first embodiment;

FIG. 7 is a top view showing the first embodiment of the invention on an injured finger and secured to a neighboring uninjured finger; and FIG. 8 is a side view of a second embodiment of the invention, showing gel pack material housed at the top and the bottom of the sleeve.

DETAILED DESCRIPTION OF EMBODIMENTS OF THE INVENTION

Figure 1:
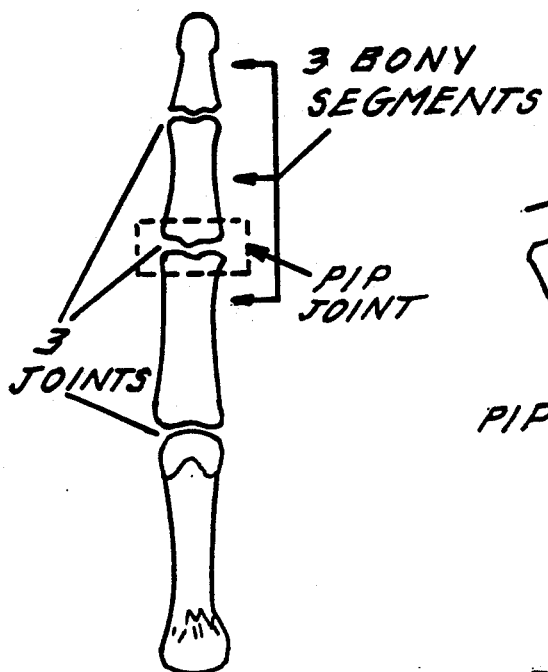
FIGS. 1 and 2 are respectively a top view and a side view of the joints of a finger, illustrating the location of a PIP joint.
Figure 2:
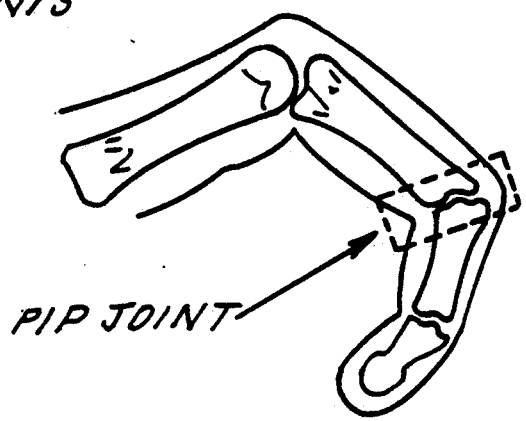
Figure 3:
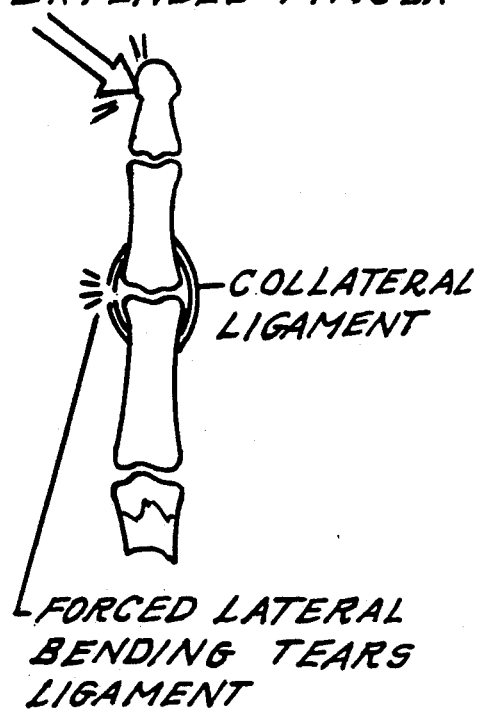
FIG. 3 is a top view of a finger schematically illustrating a PIP joint injury.
Figure 4:
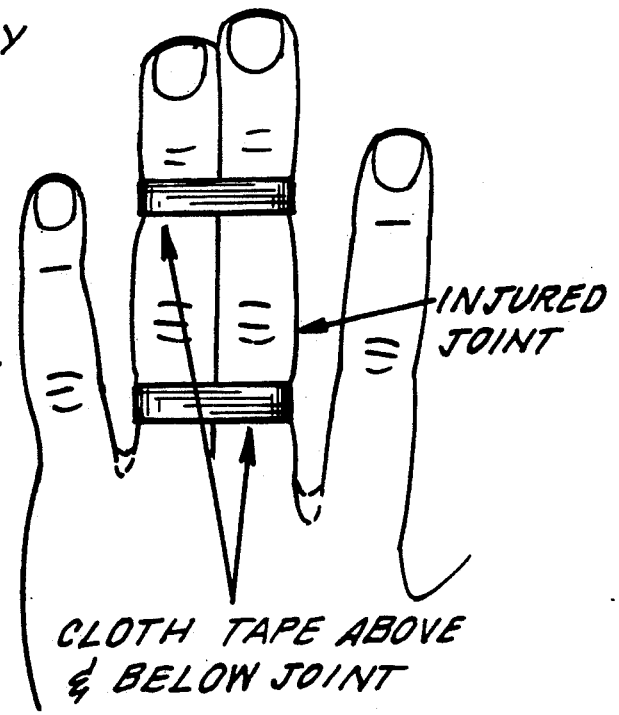
FIG. 4 is a top view of a hand illustrating the conventional method of treating a PIP joint injury.

FIGS. 5-7 show a first embodiment of the invention. The disclosed embodiment of the invention has the look and feel of an athletic garment while at the same time treating an injury. An elastic sleeve 10 is fitted over the injured finger 12 much like a stocking. It is worn so that the injured joint 14 lies beneath the midportion of the sleeve, the proximal end 16 of the sleeve hugs the base of the injured finger, and the distal end 18 lies at about the region of the distal joint of the finger (FIG. 5). The sleeve is tapered slightly to conform to the finger.

The most appropriate known material for the sleeve is a combination of 78% Nylon (TM) and 22% Spandex (TM), which is currently used in athletic sportswear. It is lightweight, comfortable and durable. The Spandex provides the elasticity which molds to the shape of the finger and does not lose its shape even after being washed several times Although not water-resistant, it dries very fast.

At either end 16, 18 of the sleeve are sewn two straps 20, 22 of 100% Nylon or another strong, water-resistant material, which are sized to wrap around the adjacent uninjured finger. Velcro (TM) hook-and-loop patches 26, 28 are provided at the ends of the straps (FIG. 6A) and fasten to corresponding patches 30, 32 on the undersurface or palmar surface 24 of the sleeve (FIG. 6B).

According to a second embodiment of the invention, a hot/cold pack is incorporated into the sleeve 10a, for example on the top side as shown in FIG. 7. The hot/cold pack may be a gel pack which is currently commercially available from Florida Medical Industries, Inc. under the trademark RECOVER (Product No. 630) for use as either a hot or a cold pack. As shown, the gel pack can be housed in a pouch within the top of the sleeve (FIG. 7). A second gel pack 40a may also be incorporated, for example on the bottom side, as shown in FIG. 8. Other locations and configurations can be employed if desired, but the front and back of the sleeve are believed to be the best location, to minimize interference with the natural motion of the fingers. The entire sleeve can then be placed in a freezer for two hours and used as both splint and ice-pack, or in hot tap water for several minutes and used as a splint and hot pack.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A finger splint for treating PIP joint injuries comprising:

an elastic sleeve sized for splinting a given finger with the PIP joint near a middle portion of the sleeve;

a pair of straps on the sleeve having two ends and being sized for extending from said sleeve on both sides of the PIP joint, around an adjacent finger, and back to said sleeve; and fastening arrangements associated with said sleeve and said straps for fastening both ends of said straps to said sleeve, said straps coacting to securely hold said splinted finger to said adjacent finger while permitting active motion of said PIP joint;

wherein said finger splint further comprises a flexible enclosure on said sleeve containing heat- and cold-retaining material in substantial contact with said splinted PIP joint for applying heat or cold to said PIP joint.

2. A finger splint as in claim 1, wherein each said fastening arrangement comprises a hook-and-loop-type fastener.

3. A finger splint as in claim 1, wherein said elastic sleeve is tapered to mold to the shape of the finger.

4. A finger splint for treating PIP joint injuries comprising:

an elastic sleeve sized for splinting a given finger with the PIP joint near a middle portion of the sleeve;

a pair of straps on the sleeve having two ends and being sized for extending from said sleeve on both sides of the PIP joint, around an adjacent finger, and back to said sleeve; and fastening arrangements associated with said sleeve and said straps for fastening both ends of said straps to said sleeve, said straps coacting to securely hold said splinted finger to said adjacent finger while permitting active motion of said splinted finger;

wherein said sleeve further comprises a flexible heat- and cold-retaining material in substantial contact with said splinted finger; and wherein said material is a fluid chemical contained in a flexible enclosure on said sleeve.

5. A finger splint as in claim 4, wherein said material is maintained in contact at least with the back and front of said splinted finger.

6. A finger splint for treating PIP joint injuries comprising an elastic sleeve sized for splinting a given finger with the PIP joint near a middle portion of the sleeve;

a pair of straps on the sleeve having two ends and being sized for extending from said sleeve on both sides of the PIP joint, around an adjacent finger, and back to said sleeve; and fastening arrangement associated with said sleeve and said straps for fastening both ends of said straps to said sleeve, said straps coacting to securely hold said splinted finger to said adjacent finger while permitting active motion of said splinted finger;

wherein said sleeve further comprises a flexible enclosure having heat- and cold-retaining material in substantial contact with said splinted finger; and wherein said material is maintained in contact at least with the back and front of said splinted finger.

* * * * *